US011510902B2

(12) United States Patent
Sheu et al.

(10) Patent No.: US 11,510,902 B2
(45) Date of Patent: Nov. 29, 2022

(54) METHOD FOR PREVENTING OR TREATING NON-ALCOHOLIC FATTY LIVER DISEASE BY ANTRODINS

(71) Applicant: Simpson Biotech Co., Ltd., Taoyuan (TW)

(72) Inventors: Chia-Chin Sheu, Taoyuan (TW); Tse-Kai Fu, Taoyuan (TW)

(73) Assignee: SIMPSON BIOTECH CO., LTD., Taoyuan (TW)

( * ) Notice: Subject to any disclaimer, the term of this patent is extended or adjusted under 35 U.S.C. 154(b) by 13 days.

(21) Appl. No.: 16/899,587

(22) Filed: Jun. 12, 2020

(65) Prior Publication Data

US 2020/0390745 A1    Dec. 17, 2020

Related U.S. Application Data

(60) Provisional application No. 62/860,257, filed on Jun. 12, 2019.

(51) Int. Cl.
*A61K 31/4015* (2006.01)
*A61P 1/16* (2006.01)

(52) U.S. Cl.
CPC ............ *A61K 31/4015* (2013.01); *A61P 1/16* (2018.01)

(58) Field of Classification Search
CPC ...... A61K 31/4015; A61K 31/341; A61P 1/16
USPC ................................................. 514/425, 473
See application file for complete search history.

(56) References Cited

U.S. PATENT DOCUMENTS 9,572,760 B2    2/2017  Huang et al.

FOREIGN PATENT DOCUMENTS

| CN | 104324023 A | * | 2/2015 |
| EP | 1634877 | | 3/2006 |
| TW | 201819620 A | * | 6/2018 |

OTHER PUBLICATIONS

Vo Duy Thong & Bui Thi Huong Quynh, Correlation of Serum Transaminase Levels with Liver Fibrosis Assessed by Transient Elastography in Vietnamese Patients with Nonalcoholic Fatty Liver Disease, International Journal of General Medicine 2021:14 1349-1355.

Giulio Marchesini of European Association for the Study of the Liver et al, Clinical Practice Guidelines, EASL-EASD-EASO Clinical Practice Guidelines for the management of non-alcoholic fatty liver disease, Journal of Hepatology 2016 vol. 64 j 1388-1402.

* cited by examiner

*Primary Examiner* — Shengjun Wang
(74) *Attorney, Agent, or Firm* — Hannah Tien (57) ABSTRACT

A method for preventing or treating a non-alcoholic fatty liver disease in a subject who is at risk of suffering from the non-alcoholic fatty liver disease or suffers from the non-alcoholic fatty liver disease, by administering to the subject a composition comprising a therapeutically effective amount of Antrodins.

2 Claims, 5 Drawing Sheets
(3 of 5 Drawing Sheet(s) Filed in Color)

METHOD FOR PREVENTING OR TREATING NON-ALCOHOLIC FATTY LIVER DISEASE BY ANTRODINS

CROSS-REFERENCES TO RELATED APPLICATIONS

The present application claims priority to U.S. Provisional Appl. No. 62/860,257, filed Jun. 12, 2019, incorporated herein by reference in its entirety.

FIELD OF THE INVENTION

The present invention relates to a method for preventing or treating a non-alcoholic fatty liver disease in a subject who is at risk of suffering from the non-alcoholic fatty liver disease or suffers from the non-alcoholic fatty liver disease, comprising administering to the subject a composition comprising a therapeutically effective amount of an extract of *Antrodia cinnamomea* mycelia or Antrodin compounds.

BACKGROUND OF THE INVENTION

Non-alcoholic fatty liver disease (NAFLD) is the most prevalent chronic liver disease in the world. NAFLD is featured with steatosis due to the accumulation of triglycerides in the liver when the rate of hepatic fatty acid uptake and hepatic fatty acid synthesis is greater than the rate of fatty acid oxidation and fatty acid export in the liver. NAFLD is highly associated with metabolic syndromes such as obesity, hyperglycemia, hypertension and dyslipidemia. About 30% of NAFLD patients are accompanied with chronic inflammation and may progress to non-alcoholic steatohepatitis (NASH). Continuous chronic inflammation results in advanced liver fibrosis, cirrhosis and hepatocellular carcinoma. Prevalent NAFLD cases are forecasted to increase by 21%, from 83.1 million (2015) to 100.9 million cases (2030), while prevalent NASH cases will increase by 63%, from 16.52 million to 27.00 million cases. The fastest-growing population of NASH patient suggests that NASH will soon supplant chronic hepatitis C or alcoholic liver disease (ALD) as the leading cause of hepatocellular carcinoma among patients waiting for a liver transplant. Reduction of hepatic fat accumulation is one of the therapeutic goals for treating NAFLD/NASH, while other approaches for treating NAFLD/NASH include reduction of oxidative stress, anti-inflammation, anti-apoptosis, anti-fibrosis/cirrhosis and microbiome modulation.

*Antrodia cinnamomea* CHANG TT & WN CHOU (Chinese name, niu-chang-chih or niu-chang-ku; synonym *Antrodia camphorata*) is a new species of the genus *Antrodia* (family Polyporaceae, Aphyllophorales) that is parasitic on the inner cavity of the endemic species *Cinnamomum kanehirai* Hay. This endangered species has been used in Taiwan to treat food, alcohol, and drug intoxication, diarrhea, abdominal pain, hypertension, skin itching and liver cancer as a Chinese folk medicine. The hot water extract of *A. cinnamomea* has hepatoprotective effect. The report showed the hepatoprotective activity of the extract of *A. cinnamomea* in mice in which hepatotoxicity is induced by *Propionibacterium acnes* (*P. acnes*)-lipopolysaccharide (LPS).

U.S. Pat. No. 7,109,232 discloses Compounds 1-5 from *Antrodia cinnamomea* mycelia and their uses such as hepatoprotection, anti-inflammation or anti-tumor activity. The above Compounds 1-5 are renamed as Antrodins A-E in another article (Phuong do T et al., 2009, inhibitory effects of Antrodins A-E from *Antrodia cinnamomea* and their metabolites on hepatitis C virus protease. Phytother Res. April; 23(4):582-4). According to these two prior arts, the Compounds 1-5 from *Antrodia cinnamomea* mycelia not only have similar structures but also have similar activities.

U.S. Pat. No. 7,732,482 discloses a method of treating fibrosis in a mammal by compounds from mycelium of *Antrodia cinnamomea*, wherein the fibrosis is mediated by TGF-$\beta$, and the TGF-$\beta$ is associated with progression of chronic liver diseases through inflammation. However, there is no report for using Antrodins to treat NAFLD/NASH by reducing the accumulation of fat droplets or triglyceride level in liver, which is the route leading to NAFLD.

SUMMARY OF THE INVENTION

The present invention provides a method for preventing or treating a non-alcoholic fatty liver disease in a subject who is at risk of suffering from the non-alcoholic fatty liver disease or suffers from the non-alcoholic fatty liver disease, comprising administering to the subject a composition comprising a therapeutically effective amount of an extract of *Antrodia cinnamomea* mycelia or Antrodin compounds.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

The present invention demonstrates that an extract of *Antrodia cinnamomea* mycelia or Antrodin compounds can treat a non-alcoholic fatty liver disease by reducing the size of lipid droplets in the liver, the liver weight, the expression of liver function markers, other related metabolic indexes and the amount of lipid deposited in the liver.

The term "a" or "an" as used herein is to describe elements and ingredients of the present invention. The term is used only for convenience and providing the basic concepts of the present invention. Furthermore, the description should be understood as comprising one or at least one, and unless otherwise explicitly indicated by the context, singular terms include pluralities and plural terms include the singular. When used in conjunction with the word "comprising" in a claim, the term "a" or "an" may mean one or more than one.

The term "or" as used herein may mean "and/or."

The present invention provides a method for preventing or treating a non-alcoholic fatty liver disease in a subject who is at risk of suffering from the non-alcoholic fatty liver disease or suffers from the non-alcoholic fatty liver disease, comprising administering to the subject a composition comprising a therapeutically effective amount of an extract of *Antrodia cinnamomea* mycelia.

In one embodiment, the extract of *Antrodia cinnamomea* mycelia is a water or organic solvent extract of *Antrodia cinnamomea* mycelia. In a preferred embodiment, the organic solvent is alcohol, ester, alkane or halogenated alkane. In a more preferred embodiment, the alcohol is ethanol.

In one embodiment, the extract of *Antrodia cinnamomea* mycelia comprises Antrodin compounds. In a preferred embodiment, the Antrodin compounds comprise Antrodin A, Antrodin B, Antrodin C, Antrodin D and Antrodin E. In a more preferred embodiment, the Antrodin compounds comprise Antrodin B, Antrodin C and Antrodin D. In another embodiment, the Antrodin compounds comprise Antrodin B and Antrodin C. In a preferred embodiment, the Antrodin compounds comprise Antrodin D and Antrodin E.

The present invention also provides a method for preventing or treating a non-alcoholic fatty liver disease in a subject who is at risk of suffering from the non-alcoholic fatty liver disease or suffers from the non-alcoholic fatty liver disease, comprising administering to the subject a composition comprising a therapeutically effective amount of a compound having the formula (I):

(I)

or its tautomeric forms, its stereoisomers, its racemates, it metabolites, its polymorphs, its salts, or its solvates, wherein X is N or O;

$R_1$ is H, hydroxyl, $C_{1-10}$ alkyloxy, $C_{2-10}$ alkenyloxy, or $C_{2-10}$ alkynyloxy;

$R_2$ is H, hydroxyl, $C_{1-10}$ alkyl, $C_{2-10}$ alkenyl or $C_{2-10}$ alkynyl;

$R_3$ is absent, H, hydroxyl, $C_{1-10}$ alkyl, $C_{2-10}$ alkenyl or $C_{2-10}$ alkynyl;

==== denotes a single or double bond;

provided that when X is O, $R_3$ is absent;

when ==== denotes a single bond, the compound has the formula of:

As used herein, the term "non-alcoholic fatty liver disease (NAFLD)" refers to fatty acid disease patients suffer from which have no history of alcohol consumption or alcohol consumption is not related to the occurrence of the fatty liver disease. The fatty liver refers to a phenomenon in which there is excessive accumulation of triglyceride in liver cells, as compared to normal levels of triglyceride. About 5% of a normal liver consists of fat tissues and the main components of the fat are triglycerides, fatty acids, phospholipids, cholesterols, and cholesterol esters. However, once a fatty liver is developed, most of the components of the fat are replaced with triglycerides. If the amount of triglycerides is more than 5% of the liver weight, it is diagnosed as fatty liver. The fatty liver is caused by a lipid metabolism disorder or a defect in the process of carrying excessive fat in the liver cells out of the liver, and is mainly caused by disorders of lipid metabolism in the liver. Most of the fat accumulated in the fatty liver is triglyceride. The non-alcoholic fatty liver disease comprises non-alcoholic fatty liver, nonalcoholic steatohepatitis, cirrhosis, liver cancer, and the likes, and the fatty liver disease to be prevented or treated with the composition of the present invention is included without limitation. In a preferred embodiment, the non-alcoholic fatty liver disease comprises nonalcoholic fatty liver and nonalcoholic steatohepatitis.

As used herein, the term "preventing" refers to all of the actions by which the non-alcoholic fatty liver disease is ameliorated or delayed by administration of the composition of the present invention.

As used herein, the term "treating" refers to therapeutic treatments that reverse, alleviate, ameliorate, inhibit, slow down or stop the progression or severity of a condition associated with a disease or disorder, e.g., NAFLD. The term "treating" includes reducing or alleviating at least one adverse effect or symptom of a condition, disease or disorder associated with NAFLD. Treatment is generally "effective" if one or more symptoms or clinical markers are reduced. Alternatively, treatment is "effective" if the progression of a disease is reduced or halted. That is, "treatment" includes not just an improvement of symptoms or markers, but also a cessation of, or at least slowing of progression or worsening of symptoms compared to what would be expected in the absence of treatment. Beneficial or desired clinical results include, but are not limited to, alleviation of one or more symptom(s), diminishment of extent of disease, stabilizing (i.e., not worsening) state of disease, delay or slowing of disease progression, amelioration or palliation of the disease state, remission (whether partial or total), reduced interventions, shortened hospital stays, and/or decreased mortality, whether detectable or undetectable. The term "treatment" of a disease also includes providing relief from the symptoms or side-effects of the disease (including palliative treatment). Treatment in this context does not include or encompass a complete "cure."

In one embodiment, the compound is an Antrodin compound. In a preferred embodiment, the Antrodin compound is selected from the group consisting of Antrodin A (3-isobutyl-4-[4-(3-methyl-2-butenyloxy)phenyl]furan-2,5-dione), Antrodin B (3-isobutyl-4-[4-(3-methyl-2-butenyloxy)phenyl]-1H-pyrrol-2,5-dione), Antrodin C (3-isobutyl-4-[4-(3-methyl-2-butenyloxy)phenyl]-1H-pyrrol-1-ol-2,5-dione), Antrodin D (3R*,4S*-1-hydroxy-3-isobutyl-4-[4-(3-methyl-2-butenyloxy)phenyl]pyrrolidine-2,5-dione), and Antrodin E (3R*,4R*-1-hydroxy-3-isobutyl-4-[4-(3-methyl-2-butenyloxy)phenyl]pyrrolidine-2,5-dione). In a more preferred embodiment, the Antrodin compound is selected from the group consisting of Antrodin B, Antrodin C, and Antrodin D.

In another embodiment, the Antrodin compound comprises Antrodin B, Antrodin C or a combination thereof. In a preferred embodiment, the Antrodin compound comprises Antrodin D, Antrodin E or racemates thereof.

In one embodiment, the therapeutically effective amount of the extract of *Antrodia cinnamomea* mycelia is sufficient to treat the non-alcoholic fatty liver disease by reducing the amount of lipid deposited in the liver. In a preferred embodiment, the therapeutically effective amount of the compound is sufficient to treat the non-alcoholic fatty liver disease by reducing the amount of lipid deposited in the liver.

In another embodiment, the therapeutically effective amount of the extract of *Antrodia cinnamomea* mycelia is sufficient to treat the non-alcoholic fatty liver disease by reducing the liver function markers. In a preferred embodiment, the therapeutically effective amount of the compound is sufficient to treat the non-alcoholic fatty liver disease by reducing the liver function markers.

In one embodiment, the therapeutically effective amount of the extract of *Antrodia cinnamomea* mycelia is sufficient to treat the non-alcoholic fatty liver disease by decreasing the related indexes of metabolic syndrome. In a preferred embodiment, the therapeutically effective amount of the compound is sufficient to treat the non-alcoholic fatty liver disease by decreasing the related indexes of metabolic syndrome. In a more preferred embodiment, the related indexes of metabolic syndrome comprise blood sugar, aspartate aminotransferase (AST), alanine aminotransferase (ALT), total cholesterol (TC) or total triglyceride (TG).

In another embodiment, the compound further treats a fatty liver related metabolic disease. In a preferred embodiment, the fatty liver related metabolic disease comprises diabetes. In a more preferred embodiment, the therapeutically effective amount of the compound is sufficient to treat the fatty liver related metabolic disease by decreasing blood sugar and the expression of insulin.

In one embodiment, the compound further inhibits inflammatory responses caused by the non-alcoholic fatty liver disease. In a preferred embodiment, the compound is sufficient to inhibit the inflammatory responses caused by the non-alcoholic fatty liver disease by decreasing the expression of malondialdehyde.

In one embodiment, the therapeutically effective amount of the compound is sufficient to treat the non-alcoholic fatty liver disease by decreasing the expressions of insulin and malondialdehyde.

In one embodiment, the subject is an animal, preferably a mammal, more preferably a human.

In one embodiment, the composition is a pharmaceutical composition. In a preferred embodiment, the pharmaceutical composition can optionally include a carrier, such as a pharmaceutically acceptable carrier. In a preferred embodiment, the pharmaceutical composition further comprises a pharmaceutically acceptable carrier. Pharmaceutically acceptable carriers are determined in part by the particular composition being administered, as well as by the particular method used to administer the composition. Accordingly, there is a wide variety of suitable formulations of the pharmaceutical compositions. Formulations suitable for parenteral administration can be formulated, for example, for intravenous, intramuscular, intradermal, intraperitoneal, and subcutaneous routes. The pharmaceutically acceptable carriers can include aqueous isotonic sterile injection solutions, which can contain antioxidants, buffers, bacteriostatic agents, and solutes that render the formulation isotonic with the blood of the intended recipient, and aqueous and non-aqueous sterile suspensions that can include suspending agents, solubilizers, thickening agents, stabilizers, preservatives, liposomes, microspheres and emulsions. The term "pharmaceutically acceptable" refers to compounds and compositions which can be administered to mammals without undue toxicity.

The composition (comprising the extract of *Antrodia cinnamomea* mycelia or the compound) and a pharmaceutically acceptable carrier can be administered to a subject through a number of different routes known in the art. In one embodiment, the composition and a pharmaceutically acceptable carrier are administered externally, intravenously, subcutaneously, topically, orally or by muscle or inhalation. The pharmaceutical composition is delivered to target sites by the digestive system or the circulatory system.

The composition (including the extract of *Antrodia cinnamomea* mycelia or the compound) and a pharmaceutically acceptable carrier may be formulated via sterile aqueous solutions or dispersions, aqueous suspensions, oil emulsions, water in oil-in-oil emulsions, specific emulsification liquids, long residence emulsifiers, viscous emulsions, microemulsions, nanoemulsions, liposomes, microparticles, microspheres, nano spheres, nanoparticles, micromercury, and several sustainable releases of natural or synthetic polymers. The pharmaceutically acceptable carrier and the composition can also be prepared as aerosols, tablets, pills, capsules, sterile powders, suppositories, lotions, creams, ointments, pastes, gels, hydrogels, sustained delivery devices, or other formulations which may be used for drug delivery.

The term "therapeutically effective amount" used herein is a therapeutic dose which can prevent, decrease, stop or reverse a symptom developed in a subject under specific conditions, or partially, completely alleviate symptoms already exist under specific conditions when the subject begins receiving the treatment.

In one embodiment, the therapeutically effective amount of the extract of *Antrodia cinnamomea* mycelia ranges from 0.01 mg/Kg to 100 mg/Kg. In a preferred embodiment, the therapeutically effective amount of the extract of *Antrodia cinnamomea* ranges from 0.05 mg/Kg to 80 mg/Kg. In a more preferred embodiment, the therapeutically effective amount of the extract of *Antrodia cinnamomea* ranges from 0.1 mg/Kg to 50 mg/Kg.

In another embodiment, the therapeutically effective amount of the compound ranges from 0.01 mg/Kg to 100 mg/Kg. In a preferred embodiment, the therapeutically effective amount of the compound ranges from 0.05 mg/Kg to 80 mg/Kg. In a more preferred embodiment, the therapeutically effective amount of the compound ranges from 0.1 mg/Kg to 50 mg/Kg.

The present invention further provides an use of a composition for preparing a drug for preventing or treating non-alcoholic fatty liver disease (NAFLD), wherein the composition comprises an extract of *Antrodia cinnamomea* mycelia.

In one embodiment, the extract of *Antrodia cinnamomea* mycelia is a water or organic solvent extract of *Antrodia cinnamomea* mycelia. In a preferred embodiment, the organic solvent is alcohol, ester, alkane or halogenated alkane. In a more preferred embodiment, the alcohol is ethanol.

In one embodiment, the extract of *Antrodia cinnamomea* mycelia comprises Antrodin compounds. In a preferred embodiment, the Antrodin compounds comprise Antrodin A, Antrodin B, Antrodin C, Antrodin D and Antrodin E. In a more preferred embodiment, the Antrodin compounds comprise Antrodin B, Antrodin C and Antrodin D. In another embodiment, the Antrodin compounds comprise Antrodin B and Antrodin C. In a preferred embodiment, the Antrodin compounds comprise Antrodin D and Antrodin E.

The present invention also provides an use of a composition for preparing a drug for preventing or treating non-alcoholic fatty liver disease (NAFLD), wherein the composition comprises a therapeutically effective amount of a compound having the formula (I):

(I)

or its tautomeric forms, its stereoisomers, its racemates, it metabolites, its polymorphs, its salts, or its solvates, wherein X is N or O;

$R_1$ is H, hydroxyl, $C_{1-10}$ alkyloxy, $C_{2-10}$ alkenyloxy, or $C_{2-10}$ alkynyloxy;

$R_2$ is H, hydroxyl, $C_{1-10}$ alkyl, $C_{2-10}$ alkenyl or $C_{2-10}$ alkynyl;

$R_3$ is absent, H, hydroxyl, $C_{1-10}$ alkyl, $C_{2-10}$ alkenyl or $C_{2-10}$ alkynyl;

===== denotes a single or double bond;

provided that when X is O, $R_3$ is absent;

when ===== denotes a single bond, the compound has the formula:

In one embodiment, the non-alcoholic fatty liver disease comprises nonalcoholic fatty liver and nonalcoholic steatohepatitis.

In one embodiment, the compound is an Antrodin compound. In a preferred embodiment, the Antrodin compound is selected from the group consisting of Antrodin A, Antrodin B, Antrodin C, Antrodin D, and Antrodin E. In a more preferred embodiment, the Antrodin compound is selected from the group consisting of Antrodin B, Antrodin C, and Antrodin D.

In another embodiment, the Antrodin compound comprises Antrodin B, Antrodin C or a combination thereof. In a preferred embodiment, the Antrodin compound comprises Antrodin D, Antrodin E or racemates thereof.

In one embodiment, the therapeutically effective amount of the extract of *Antrodia cinnamomea* mycelia treats the non-alcoholic fatty liver disease by reducing the amount of lipid deposited in the liver. In a preferred embodiment, the therapeutically effective amount of the compound treats the non-alcoholic fatty liver disease by reducing the amount of lipid deposited in the liver.

In another embodiment, the therapeutically effective amount of the extract of *Antrodia cinnamomea* mycelia treats the non-alcoholic fatty liver disease by reducing the liver function markers. In a preferred embodiment, the therapeutically effective amount of the compound treats the non-alcoholic fatty liver disease by reducing the liver function markers.

In one embodiment, the therapeutically effective amount of the extract of *Antrodia cinnamomea* mycelia treats the non-alcoholic fatty liver disease by decreasing the related indexes of metabolic syndrome. In a preferred embodiment, the therapeutically effective amount of the compound treats the non-alcoholic fatty liver disease by decreasing the related indexes of metabolic syndrome. In a more preferred embodiment, the related indexes of metabolic syndrome comprise blood sugar, ALT, AST, TG or TC.

In another embodiment, the compound further treats a fatty liver related metabolic disease. In a preferred embodiment, the fatty liver related metabolic disease comprises diabetes. In a more preferred embodiment, the therapeutically effective amount of the compound treats the fatty liver related metabolic disease by decreasing blood sugar and the expression of insulin.

In one embodiment, the compound further inhibits inflammatory responses caused by the non-alcoholic fatty liver disease. In a preferred embodiment, the compound inhibits the inflammatory responses caused by the non-alcoholic fatty liver disease by decreasing the expression of malondialdehyde.

In one embodiment, the therapeutically effective amount of the compound treats the non-alcoholic fatty liver disease by decreasing the expressions of the insulin and malondialdehyde.

In one embodiment, the composition is a pharmaceutical composition. In a preferred embodiment, the pharmaceutical composition further comprises a pharmaceutically acceptable carrier. The pharmaceutical composition is delivered to target sites by the digestive system or the circulatory system.

In one embodiment, the therapeutically effective amount of the extract of *Antrodia cinnamomea* mycelia ranges from 0.01 mg/Kg to 100 mg/Kg. In a preferred embodiment, the therapeutically effective amount of the extract of *Antrodia cinnamomea* ranges from 0.05 mg/Kg to 80 mg/Kg. In a more preferred embodiment, the therapeutically effective amount of the extract of *Antrodia cinnamomea* ranges from 0.1 mg/Kg to 50 mg/Kg.

In another embodiment, the therapeutically effective amount of the compound ranges from 0.01 mg/Kg to 100 mg/Kg. In a preferred embodiment, the therapeutically effective amount of the compound ranges from 0.05 mg/Kg to 80 mg/Kg. In a more preferred embodiment, the therapeutically effective amount of the compound ranges from 0.1 mg/Kg to 50 mg/Kg.

Examples

The examples below are non-limiting and are merely representative of various aspects and features of the present invention.

Material and Methods

1 Inhibition of Lipid Accumulation in Cells 1.1 Cell Culture

Human hepatoma cell line Hep G2 was cultured in Dulbecco's modified Eagle's medium high glucose (DMEM-HG) containing 10% fetal bovine serum, 100 U/ml penicillin and 100 mg/ml streptomycin at 37° C. under 5% $CO_2$ in an incubator.

1.2 Cell Viability Test

Hepasim® was a mixture from *Antrodia cinnamomea* mycelia, which was prepared from water or organic solvent extract of *Antrodia cinnamomea* mycelia. The extract of *Antrodia cinnamomea* mycelia comprised Antrodin B-E. $5 \times 10^3$ Hep G2 cells were seeded in a 96-well plate for 24 hrs, and then incubated with different concentrations of Hepasim®, Antrodin B, Antrodin C and Antrodin D for 72 hrs. After treatment, cells were incubated with alamar blue (10%, w/v) for 3 hrs, and then was read at 540 and 630 nm. Cell viability was calculated by $[(OD570-OD600)_{test}/(OD570-OD600)_{control}] \times 100$.

1.3 Free Fatty Acids (FFA)-Induced Lipid Accumulation and Oil Red Determination $1 \times 10^5$ Hep G2 cells were seeded in a 96-well plate and incubated with serum-free cellular medium containing 1% BSA for 24 hrs. To induce lipid accumulation, the above cells were seeded in a mixture of 0.33 mM palmitic acid and 0.66 mM oleic acid for 24 hrs, which were dissolved in serum-free medium with or without Antrodin. After lipid accumulation and Antrodin treatment, cells were washed with PBS and then fixed by 4% paraformaldehyde for 15 mins at room temperature. The fixed cells were washed with PBS for 5 mins, and then rinsed with 60% isopropanol twice; followed by incubation with 1 ml Oil Red kit for 10 mins. For quantitative analysis of cellular lipids, dye in the cellular lipids were extracted with 0.5 ml of isopropanol, and then measured at 490 nm.

2 Improvement of Fatty Liver Disease Correlated Indexes in Animal Model 2.1 8-week-old male C57BL/6J (B6) mice were used, which were purchased from the National Laboratory Animal Center (Taipei, Taiwan). All animals were maintained at an animal room at a temperature of 23±2° C., and 12 hrs light/12 hrs dark cycle.

2.2 Animal Group

According to the "Healthy food of liver health effects assessment" (Taiwan Food and Drug Administration, Taiwan), all 8-week test mice were randomized into a control group, a high fat diet group, and test (high fat diet with different dosage of Hepasim®, Antrodin B or Antrodin C) groups. Each group contained 3-4 mice.

2.3 Test Method (Preventing Process)

The control group was given 18 weeks of normal diet, and other groups were given 18 weeks of high fat diet. The control group and the high fat diet group were given oral gavage of deionized water, and the Hepasim group was given oral gavage of 30 mg/Kg of Hepasim® every day. Body weights of the mice in each group were recorded weekly. At the end of 18 weeks, all mice were sacrificed by $CO_2$ overdose. At the time of death of the mouse, blood was collected from the heart of the mouse. To separate the serum, whole blood was centrifuged in a refrigerated centrifuge at 15,700×g at 4° C. for 5 minutes. The liver was removed from the mouse, and then rinsed in ice-cold saline. Liver samples were divided for various assays and histological assessment.

2.4 Test Method (Treating Process)

The control group was given 20 weeks of normal diet, and all other groups were given 20 weeks of high fat diet. The control group and the high fat diet group were given oral gavage of deionized water, and the Antrodin B or Antrodin C group was given oral gavage of 10 or 30 mg/Kg of Antrodin B or Antrodin C every day from $11^{th}$ to $20^{th}$ week. Body weights of the mice in each group were recorded weekly. At the end of 20 weeks, all mice were sacrificed by $CO_2$ overdose. At the time of death of the mouse, blood was collected from the heart of the mouse. To separate the serum, whole blood was centrifuged in a refrigerated centrifuge at 15,700×g at 4° C. for 5 minutes. Livers were removed from the mice, and then rinsed in ice-cold saline. Liver samples were divided for various assays and histological assessment.

2.5 Determination Method of Each Index

Stored liver samples (0.1 g) were homogenized in 1 ml PBS, and then was centrifuged in a refrigerated centrifuge at 15,700×g at 4° C. for 5 minutes to remove pellets. The levels of aspartate aminotransferase (AST), alanine aminotransferase (ALT), total cholesterol (TC) and total triglyceride (TG) of the serum and the liver were measured by corresponding detection kits (Randox). Blood sugar in whole blood was detected by blood sugar machine (Roche). Plasma insulin was detected by Insulin mouse ELISA kit (Invitrogen). Malondialdehyde (MDA) level in liver was measured by using Lipid Peroxidation Assay Kit (Colorimetric/Fluorometric) (abcam, #ab118977). Liver samples were divided for various assays and histological assessment.

2.6 Histological Assessment

The livers were removed from the mice, and then fixed in 10% neural formalin. Liver samples were dehydrated by placing in ethanol at different concentrations (30, 50, 70, 95, 99.5%) and xylene. Finally, liver samples were embedded in paraffin section. For hematoxylin-eosin staining, the liver tissue sections were placed in xylene for 30 minutes for dewaxing, and then sequentially placed in 99.5% ethanol for 10 minutes, 90% ethanol for 5 minutes, 70% ethanol for 1 minute, 50% ethanol for 1 minute and 30% ethanol for 1 minutes for rehydration, and then soaked in distilled water for 10 minutes. To stained nuclei, the samples were soaked in hematoxylin solution for 4 minutes, and then soaked in distilled water for several minutes, followed by soaking in eosin solution for 2 minutes to stain cytoplasm, and then washed in distilled water for 10 minutes. Finally, samples were sequentially placed in 90% ethanol for 2 minutes, 99.5% ethanol for 2 minutes and xylene for 20 minutes, and then mounted by mounting medium.

2.7 Statistical Analysis

All results were expressed as mean±SD. Significant differences were analyzed with two-tailed Student's t-test. $P<0.05$ represents the statistical difference between two groups.

Results

1 Inhibition of Lipid Accumulation in Cell 1.1 Cell Viability Test

Figure 1:
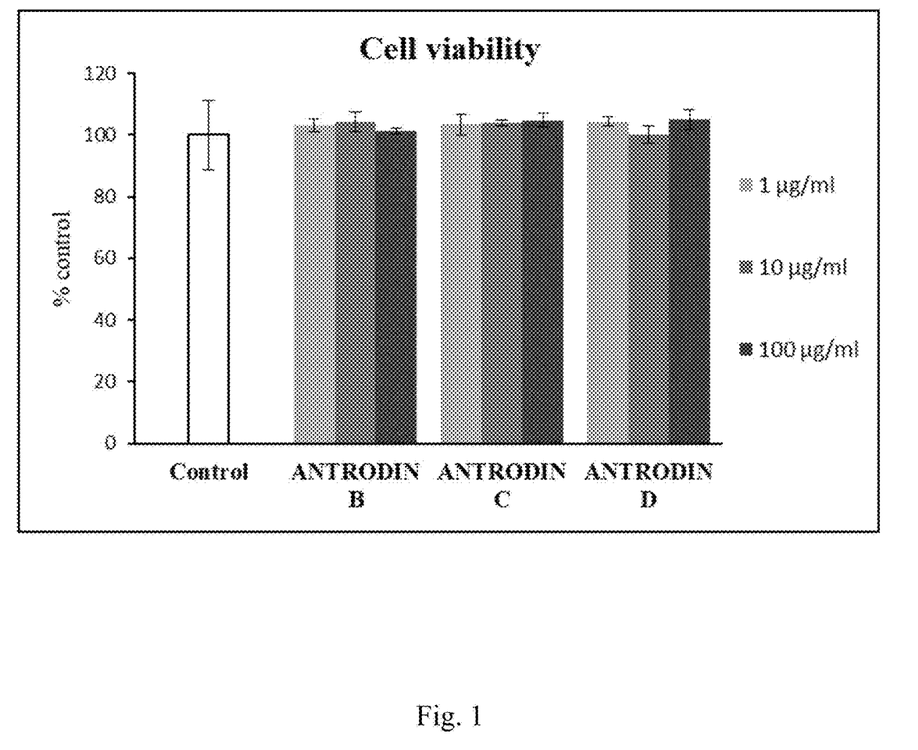
FIG. 1 shows cell viability of Hep G2 cells treated with Antrodin at a concentration less than 100 µg/ml.

With alamar blue treatment, all groups showed no significant difference of absorbance value as compared with the control group (FIG. 1). This result indicated that Hepasim®, Antrodin B, Antrodin C and Antrodin D had no cytotoxicity to Hep G2 cells at a concentration less than 100 μg/ml.

1.2 Oil Red Assay

Oil Red assay is a method for directly detecting lipid accumulation in cell. The cells in all groups were incubated with free fatty acid to induce cellular lipid accumulation. Compared with a blank group which was not incubated with free fatty acid to induce cellular lipid accumulation, the control group increased 60% of lipid in the cells.

Figure 2:
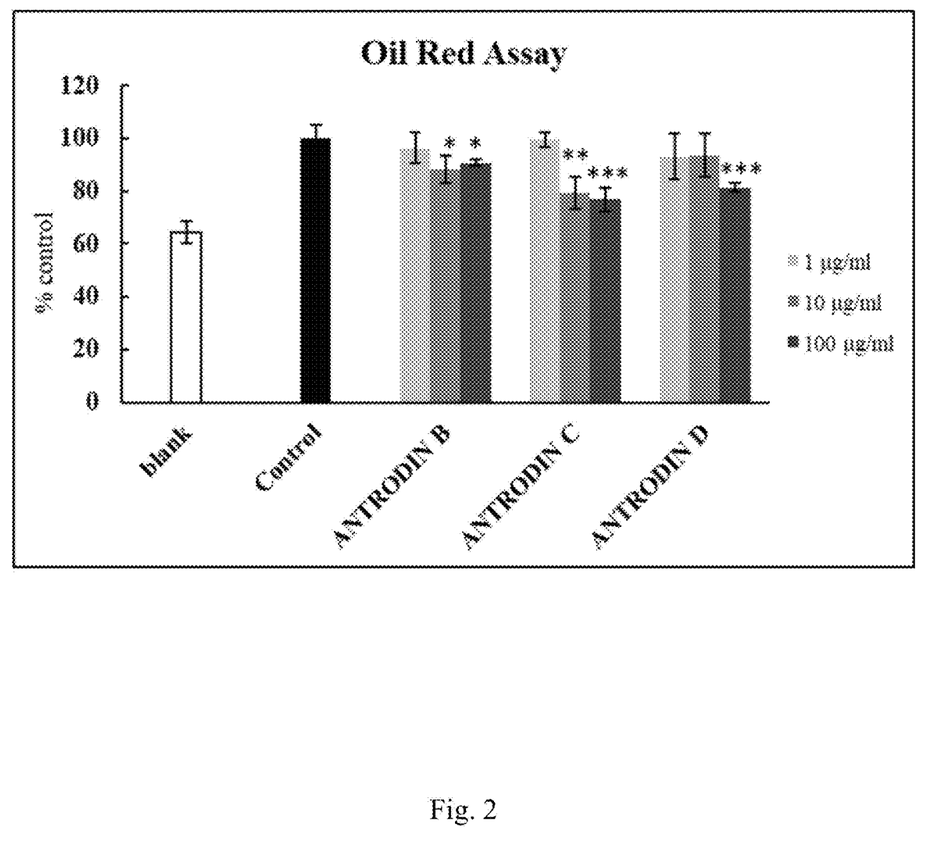
FIG. 2 shows lipid accumulation in free fatty acid-induced Hep G2 cells treated with Antrodin.

In the test groups, Antrdin B, Antrodin C and Antrodin D significantly reduced cellular lipid accumulation as compared with the control group (FIG. 2). 10 μg/ml and 100 μg/ml of Antrodin B respectively attenuated 12.8% and 9.3% of lipid accumulation in the cells; 10 μg/ml and 100 μg/ml of Antrodin C respectively attenuated 20.6% and 24.1% of lipid accumulation in the cells; 100 μg/ml of Antrodin D attenuated 18.6% of lipid accumulation in the cells.

2 Improvement of Fatty Liver Disease Correlated Index in Animal Model 2.1 Hepasim® Significantly Reduced the Increased Body Weight and Liver Weight Caused by High Fat Diet Both body weight and liver weight increased in the high fat diet group as compared with the control group (normal diet). In the test group, feeding mice on high fat diet with 30 mg/Kg of Hepasim® could significantly reduce the increased body weight and liver weight caused by the high fat diet. At the end of 14 weeks, the body weight and liver weight of Hepasim group decreased by 32.7% and 35.2 as compared with the high fat diet group, respectively. All data were shown in Table 1.

TABLE 1

Body weight and liver weight after administration (preventing process)

| Group | body weight (g) | liver weight (g) | liver weight/ body weight |
|---|---|---|---|
| Control | 30.6 ± 0.65 | 1.32 ± 0.09 | 4.49 ± 0.40 |
| High fat diet | 46.5 ± 1.49 | 1.74 ± 0.16 | 3.77 ± 0.45 |
| High fat diet with 30 mg/Kg Hepasim ® | 30.8 ± 3.09 | 1.13 ± 0.05 | 3.64 ± 0.05 |

2.2 the Fatty Liver Disease Correlated Indexes were Significantly Improved by Treatment with Hepasim®

The serum levels of ALT, AST, TG, TC in the high fat diet group had rapid gain as compared with the control group, while Hepasim® attenuated the increased ALT, AST, TG, TC induced by the high fat diet by about 68%, 70%, 28.8%, and 27.5%, respectively, as compared with the high fat diet group. Moreover, Hepasim® significantly decreased the levels of TG and TC in the liver by about 28.8% and 20.6%, respectively. All values were shown in Table 2 and 3.

TABLE 2

ALT, AST, TG and TC in serum after administration (preventing process)

| Group | Serum ALT (IU/l) | Serum AST (IU/l) | Serum TG (IU/l) | Serum TC (IU/l) |
|---|---|---|---|---|
| Control | 19.81 ± 0.93 | 33.62 ± 6.12 | 127.54 ± 6.55 | 160.11 ± 10.88 |
| High fat diet | 89.29 ± 12.53 | 130.48 ± 16.38 | 170.68 ± 10.03 | 233.08 ± 24.88 |
| High fat diet with 30 mg/Kg Hepasim ® | 29.01 ± 5.32 | 38.33 ± 8.46 | 118.02 ± 6.88 | 168.94 ± 17.72 |

TABLE 3

TG and TC in liver after administration (preventing process)

| Group | liver TG (mg/dl) | liver TC (mg/dl) |
|---|---|---|
| Control | 169.66 ± 29.57 | 123.60 ± 13.15 |
| High fat diet | 222.73 ± 18.51 | 201.20 ± 5.87 |
| High fat diet with 30 mg/Kg Hepasim ® | 158.53 ± 12.46 | 95.39 ± 25.69 |

2.3 Liver Appearance and IHC of Liver Section

Figure 3:
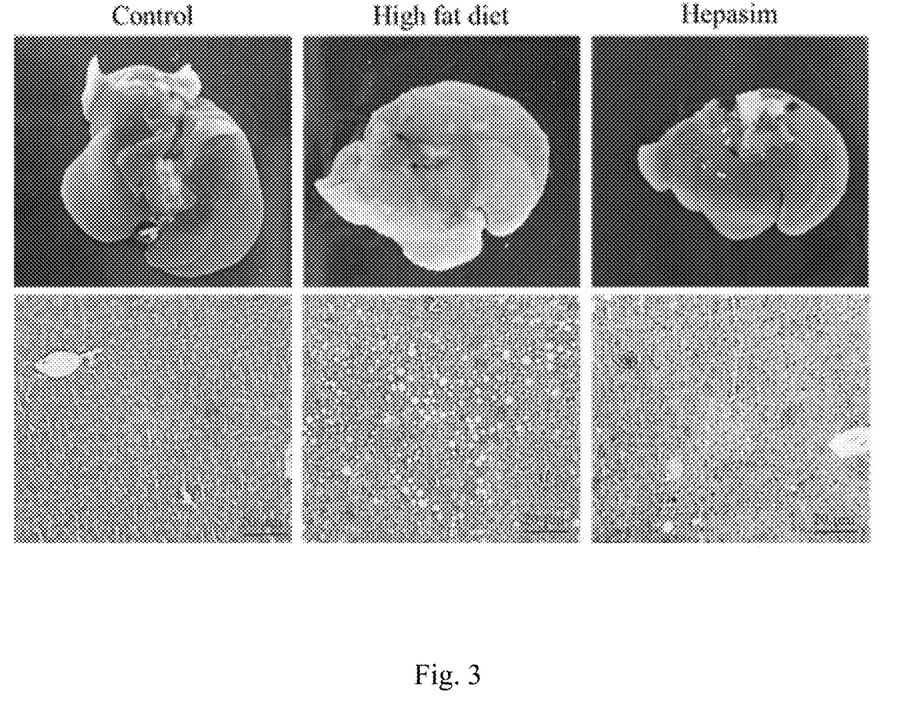
FIG. 3 shows liver appearance and H&E staining of liver sections after Hepasim® administration (×100, magnification).

The color of the livers of the mice from the high fat diet group was pale, which was a phenomenon of fatty liver as compared with the control group, but the condition was not observed in the livers of the mice from the Hepasim group. According to hematoxylin-eosin staining of the liver section, there were more lipid droplets in the livers of the mice from the high fat diet group, while Hepasim® attenuated the increased lipid droplets in the liver (FIG. 3).

3 Improvement of Fatty Liver Disease Correlated Index in Animal Model with Antrodin Treatment 3.1 Antrodin B and Antrodin C Reduced the Increased Body Weight and Liver Weight Caused by High Fat Diet Both body weight and liver weight of the mice significantly increased in the high fat diet group as compared with the control group (normal diet). At the end of 20 weeks, feeding animal on the high fat diet with 10 mg/Kg of Antrodin B, 10 mg/Kg of Antrodin C or 30 mg/Kg of Antrodin C could respectively reduce 14%, 4.5% or 12.9% of body weight increasing rate as compared with the high fat diet group. Body weight increasing rate=[(weight of each group-weight of control group)/weight of control group]*100%. Feeding with 10 mg/Kg of Antrodin B, 10 mg/Kg of Antrodin C or 30 mg/Kg of Antrodin C also significantly inhibited liver hypertrophy. All data was shown in Table 4.

TABLE 4

Body weight, bodyweight increasing rate and liver weight after administration (treating process)

| Group | body weight (g) | body weight increasing rate (%) | liver weight (g) |
|---|---|---|---|
| Control | 30.68 ± 1.34 | 0 | 1.33 ± 0.08 |
| High fat diet | 41.46 ± 6.06 | 35.1 | 1.56 ± 0.67 |
| High fat diet with 10 mg/Kg Antrodin B | 37.14 ± 5.18 | 21.1 | 1.39 ± 0.33 |
| High fat diet with 30 mg/Kg Antrodin B | 41.82 ± 2.61 | 36.3 | 1.5 ± 0.25 |
| High fat diet with 10 mg/Kg Antrodin C | 40.06 ± 4.74 | 30.6 | 1.06 ± 0.25 |
| High fat diet 30 mg/Kg Antrodin C | 37.50 ± 4.80 | 22.2 | 1.05 ± 0.24 |

3.2 the Fatty Liver Disease Correlated Indexes were Improved by Treating with Antrodin B or Antrodin C The levels of blood sugar, ALT, AST, TG and TC in the serum of the mice in the high fat diet group had significantly increased as compared with the control group, while 10 mg/Kg of Antrodin C treatment attenuated the increased blood sugar, ALT, AST, TG and TC by about 34.78%, 12.3%, 39.35%, 11.57% and 66.83%, respectively, as compared with the high fat diet group. Treating with 30 mg/Kg of Antrodin C attenuated the increased blood sugar, ALT, AST, TG and TC by about 79.48%, 48.96%, 74.17%, 21.96% and 86.26%, respectively, as compared with the high fat diet group. These results indicated that Antrodin C could significantly improve fatty liver disease. All values were shown in Table 5.

3.3 Plasma Insulin in High Fat Diet Mice was Improved by Treating with Antrodin B or Antrodin C Diabetes is highly correlated with fatty liver and many fatty liver patients also have high blood sugar symptom. It was proved that Antrodin could reduce blood sugar in high fat diet mice. Another diabetes index, plasma insulin, was also improved when treated with Antrodin B or Antrodin C. As compared with the control group, plasma insulin in high fat diet mice raised to 2.2 ng/ml from 0.5 ng/ml. When being treated with 10 mg/Kg of Antrodin B, 30 mg/Kg of Antrodin B, 10 mg/Kg of Antrodin C or 30 mg/Kg of Antrodin C, the plasma insulin level increasing rate was reduced by 223.6%, 69.1%, 81.8% or 176.3%, respectively. The plasma insulin level increasing rate=[(plasma insulin level of each group-plasma insulin level of control group)/plasma insulin level of control group]*100%. This result indicated that both Antrodin B and Antrodin C could improve fatty liver related metabolic disease including diabetes. All values were shown in Table 6.

TABLE 6

Plasma insulin level after administration (treating process)

| Group | Plasma insulin (ng/ml) | Plasma insulin increasing rate (%) |
|---|---|---|
| Control | 0.55 ± 0.08 | 0 |
| High fat diet | 2.22 ± 1.13 | 303.6 |
| High fat diet with 10 mg/Kg Antrodin B | 0.99 ± 0.41 | 80 |
| High fat diet with 30 mg/Kg Antrodin B | 1.84 ± 0.93 | 234.5 |
| High fat diet with 10 mg/Kg Antrodin C | 1.77 ± 0.85 | 221.8 |
| High fat diet with 30 mg/Kg Antrodin C | 1.25 ± 0.71 | 127.3 |

TABLE 5

Blood sugar, ALT, AST, TG and TC in serum after administration (treating process)

| Group | blood glucose (mg/dl) | AST (U/l) | ALT (U/l) | TG (mg/dl) | TC (mg/dl) |
|---|---|---|---|---|---|
| Control | 274.17 ± 49.35 | 24.20 ± 2.81 | 13.62 ± 4.23 | 105.66 ± 15.62 | 159.49 ± 18.95 |
| High fat diet | 393.20 ± 75.44 | 40.13 ± 11.73 | 29.07 ± 5.84 | 188.91 ± 4.30 | 249.54 ± 42.10 |
| High fat diet with 10 mg/Kg Antrodin B | 367.20 ± 34.40 | 44.39 ± 7.06 | 29.36 ± 6.17 | 189.57 ± 9.35 | 266.61 ± 25.99 |
| High fat diet with 30 mg/Kg Antrodin B | 389.00 ± 41.63 | 53.64 ± 9.99 | 29.38 ± 11.45 | 187.77 ± 6.53 | 287.73 ± 48.26 |
| High fat diet with 10 mg/Kg Antrodin C | 351.80 ± 85.00 | 38.17 ± 5.53 | 22.99 ± 5.15 | 179.28 ± 15.54 | 189.36 ± 58.12 |
| High fat diet with 30 mg/Kg Antrodin C | 298.60 ± 38.93 | 32.33 ± 2.85 | 17.61 ± 3.90 | 170.63 ± 13.22 | 171.86 ± 40.58 |

3.4 Oxidative Stress in High Fat Diet Mice was Improved by Treating with Antrodin B or Antrodin C Malondialdehyde (MDA), a derivate of reactive oxygen species (ROS), is a common indication of oxidative stress in the body. In this experiment, the high fat diet significantly induced MDA level by an increase of 226% in mice. This result indicated that the high fat diet increased oxidative stress in mice. When been Treated with 10% Antrodin B, 30% Antrodin B, 10% Antrodin C or 30% Antrodin C, the MDA level increasing rate was reduced by 24.8%, 129.6%, 86% or 136.7% in mice. This result indicated that Antrodin B or Antrodin C was able to improve liver disease related with inflammation by reducing oxidative stress (but not only). All values were shown in Table 7.

TABLE 7

Malondialdehyde level in liver after administration (treating process)

| Group | Malondiadehyde in liver (mmole/mg protein) | MDA level increasing rate (%) in liver |
|---|---|---|
| Control | 0.71 ± 0.13 | 0 |
| High fat diet | 2.32 ± 0.77 | 226.8 |
| High fat diet with 10 mg/Kg Antrodin B | 2.15 ± 0.58 | 202.8 |
| High fat diet with 30 mg/Kg Antrodin B | 1.4 ± 0.56 | 97.2 |
| High fat diet with 10 mg/Kg Antrodin C | 1.71 ± 0.59 | 140.8 |
| High fat diet with 30 mg/Kg Antrodin C | 1.35 ± 0.57 | 90.1 |

Figure 4:
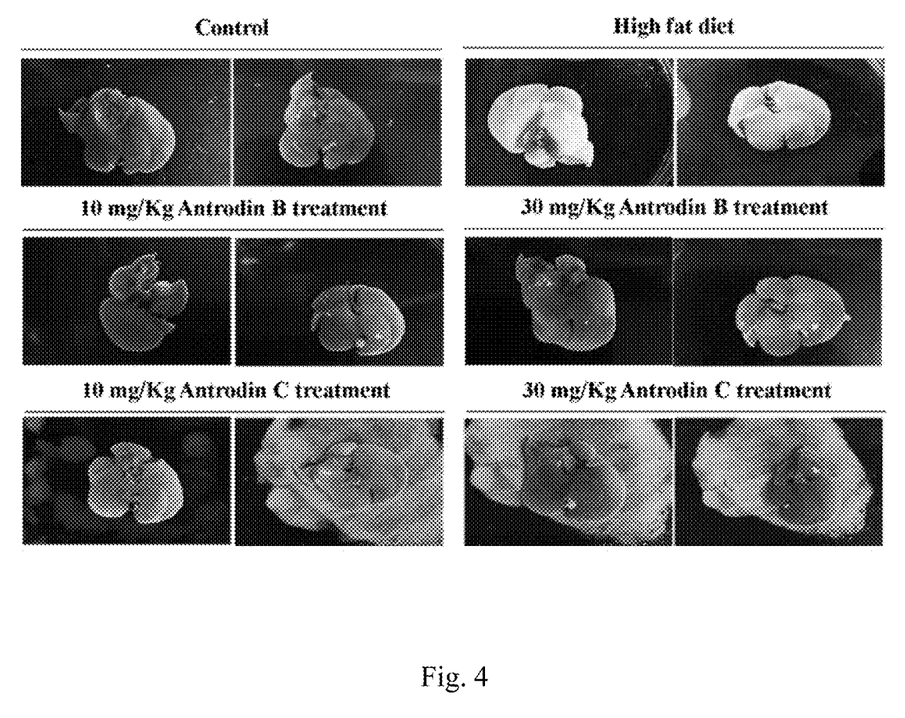
FIG. 4 shows liver appearance after Antrodin B or Antrodin C administration.
Figure 5:
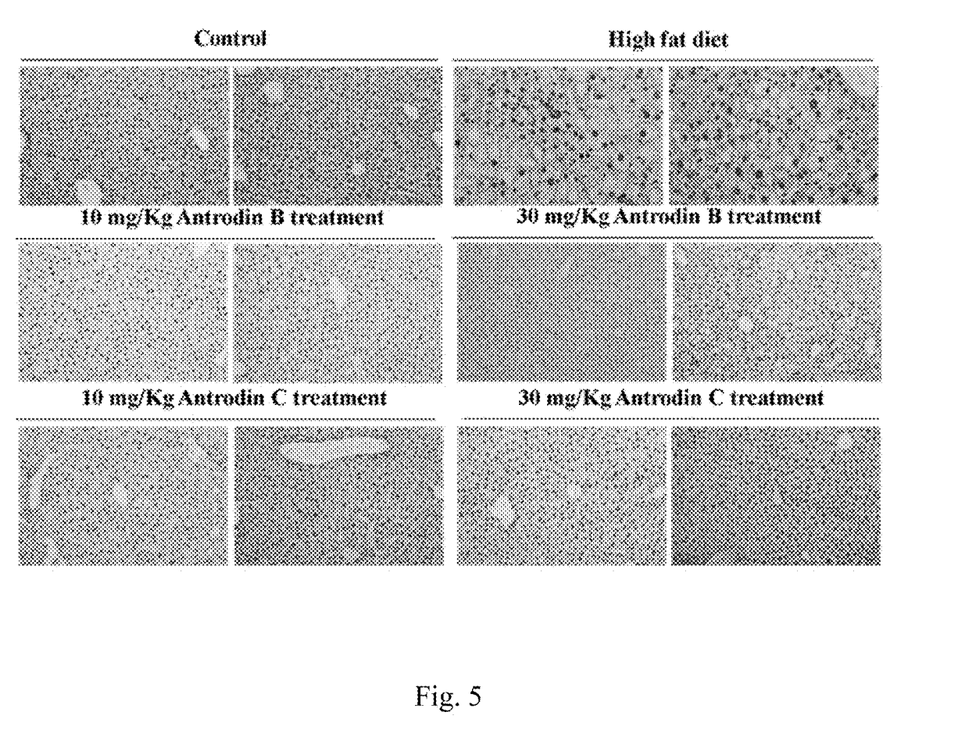
FIG. 5 shows H&E staining of liver sections after Antrodin B or Antrodin C administration (×100, magnification).

3.5 Liver Appearance and IHC of Liver Section in High Fat Diet Mice by Treating with Antrodin B or Antrodin C Hematoxylin-eosin staining of liver section or liver appearance (oil accumulation or hypertrophy) is one of the indicators for liver diseases related to inflammation or fatty liver. The color of the livers of the mice in the high fat diet group was pale, which was a phenomenon of fatty liver as compared with the control group, but the same condition was not observed in the Antrodin B or Antrodin C group (FIG. 4). According to the hematoxylin-eosin staining of the liver sections, there were more lipid droplets in the livers of the mice in the high fat diet group, but 10% Antrodin B, 30% Antrodin B, 10% Antrodin C or 30% Antrodin C, significantly attenuated the increased lipid droplets in the liver (FIG. 5). These results clearly indicated that Antrodin B or Antrodin C improved liver diseases related to inflammation or fatty liver.

The invention illustratively described herein suitably may be practiced in the absence of any element or elements, limitation or limitations, which are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method for reducing the amount of lipid deposited in the liver of a subject who is at risk of suffering from non-alcoholic fatty liver (NAFL) or suffers from non-alcoholic fatty liver (NAFL), comprising administering to the subject who is at risk of suffering from NAFL or suffers from NAFL a composition consisting of a therapeutically effective amount of 3-isobutyl-4-[4-(3-methyl-2-butenyloxy)phenyl]-1H-pyrrol-1-ol-2,5-dione, wherein the amount of fat deposited in the liver of the subject after administration is reduced.

2. The method of claim 1, wherein the therapeutically effective amount of 3-isobutyl-4-[4-(3-methyl-2-butenyloxy)phenyl]-1H-pyrrol-1-ol-2,5-dion ranges from 0.01 mg/kg to 100 mg/kg.

* * * * *